US011166801B2

(12) United States Patent
Mourhatch et al.

(10) Patent No.: US 11,166,801 B2
(45) Date of Patent: *Nov. 9, 2021

(54) HUMIDITY-MANAGEMENT PACKAGING SYSTEMS AND METHODS

(71) Applicant: Edwards Lifesciences Corporation, Irvine, CA (US)

(72) Inventors: Ryan Mourhatch, Irvine, CA (US); Gregory G. Liburd, Riverside, CA (US)

(73) Assignee: Edwards Lifesciences Corporation, Irvine, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/816,889

(22) Filed: Mar. 12, 2020

(65) Prior Publication Data
US 2020/0205959 A1    Jul. 2, 2020

Related U.S. Application Data

(63) Continuation of application No. 15/909,111, filed on Mar. 1, 2018, now Pat. No. 10,631,968.
(Continued)

(51) Int. Cl.
*A61F 2/00*       (2006.01)
*B65B 61/20*      (2006.01)
(Continued)

(52) U.S. Cl.
CPC .......... *A61F 2/0095* (2013.01); *B65B 61/20* (2013.01); *A61F 2/06* (2013.01); *A61F 2/08* (2013.01);
(Continued)

(58) Field of Classification Search
CPC .. A61F 2/0095; A61F 2/24; A61F 2/06; A61F 2/08; B65B 61/20; B65B 5/04;
(Continued)

(56) References Cited

U.S. PATENT DOCUMENTS 4,011,947 A    3/1977  Sawyer
4,101,031 A    7/1978  Cromie
(Continued)

FOREIGN PATENT DOCUMENTS

WO         9836992 A1    8/1998
WO      2008035337 A2    3/2008
WO      2014142677 A1    9/2014

OTHER PUBLICATIONS

J.F. Young. Humidity control in the laboratory using salt solutions—A review. J. Applied Chem. 1967, 17:241-245.
(Continued)

*Primary Examiner* — Michael C Miggins
(74) *Attorney, Agent, or Firm* — Darren M. Franklin; Michelle Kim; Sheppard, Mullin, Richter & Hampton, LLP

(57) ABSTRACT

Packaging systems and methods are disclosed for storing a bioprosthetic device comprising a bioprosthetic tissue and maintaining a target relative humidity across a temperature range. The packaging system includes a sealed package defining an internal space having an internal volume, and a humidity control device and bioprosthetic device within the internal space. The humidity control device includes a barrier defining an enclosed space and a humidity control solution comprising glycerol in the enclosed space. At least a portion of the barrier comprises a gas-permeable membrane. The target relative humidity is provided within the internal volume of the sealed package and the control device maintains the target relative humidity across the temperature range by selectively liberating and absorbing water vapor.

28 Claims, 6 Drawing Sheets

Related U.S. Application Data

(60) Provisional application No. 62/467,684, filed on Mar. 6, 2017.

(51) Int. Cl.

| | | |
|---|---|---|
| *B65B 5/04* | (2006.01) | |
| *B65B 7/28* | (2006.01) | |
| *B65D 81/26* | (2006.01) | |
| *A61F 2/24* | (2006.01) | |
| *A61F 2/06* | (2013.01) | |
| *A61F 2/08* | (2006.01) | |
| *B65D 81/22* | (2006.01) | |

(52) U.S. Cl.
CPC . *A61F 2/24* (2013.01); *B65B 5/04* (2013.01); *B65B 5/045* (2013.01); *B65B 7/2842* (2013.01); *B65D 81/22* (2013.01); *B65D 81/264* (2013.01)

(58) Field of Classification Search
CPC ..... B65B 7/2842; B65B 5/045; B65D 81/264; B65D 81/22
See application file for complete search history.

(56) References Cited

U.S. PATENT DOCUMENTS

| | | |
|---|---|---|
| 4,182,446 A | 1/1980 | Penny |
| 4,211,325 A | 7/1980 | Wright |
| 4,697,703 A | 10/1987 | Will |
| 4,801,015 A | 1/1989 | Lubock et al. |
| 5,035,731 A | 7/1991 | Spruill et al. |
| 5,167,223 A | 12/1992 | Koros et al. |
| 5,236,450 A | 8/1993 | Scott |
| 5,336,616 A | 8/1994 | Livesey et al. |
| 5,480,425 A | 1/1996 | Ogilive |
| 5,531,785 A | 7/1996 | Love et al. |
| 5,560,487 A | 10/1996 | Starr |
| 5,578,076 A | 11/1996 | Krueger et al. |
| 5,582,607 A | 12/1996 | Lackman |
| 5,615,770 A | 4/1997 | Applebaum et al. |
| 5,690,226 A | 11/1997 | N'Guyen |
| 5,720,391 A | 2/1998 | Dohm et al. |
| 5,776,187 A | 7/1998 | Krueger et al. |
| 5,800,531 A | 9/1998 | Cosgrove et al. |
| 5,823,342 A | 10/1998 | Caudillo et al. |
| 5,868,253 A | 2/1999 | Krueger et al. |
| 5,936,178 A | 8/1999 | Saari |
| 5,960,956 A | 10/1999 | Langanki et al. |
| 5,980,569 A | 11/1999 | Scirica |
| 5,984,959 A | 11/1999 | Robertson et al. |
| 6,090,138 A | 7/2000 | Chasak et al. |
| 6,126,007 A | 10/2000 | Kari et al. |
| 6,197,053 B1 | 3/2001 | Cosgrove et al. |
| 6,199,696 B1 | 3/2001 | Lytle et al. |
| 6,346,094 B2 | 2/2002 | West et al. |
| 6,416,547 B1 | 7/2002 | Erickson et al. |
| 6,534,004 B2 | 3/2003 | Chen et al. |
| 6,591,998 B2 | 7/2003 | Haynes et al. |
| 6,723,122 B2 | 4/2004 | Yang et al. |
| 6,736,845 B2 | 5/2004 | Marquez et al. |
| 6,966,925 B2 | 11/2005 | Stobie |
| 7,389,874 B2 | 6/2008 | Quest et al. |
| 7,699,168 B2 | 4/2010 | Ryan et al. |
| 7,712,606 B2 | 5/2010 | Salahieh et al. |
| 7,866,468 B2 | 1/2011 | Kyritsis |
| 8,136,659 B2 | 3/2012 | Salahieh et al. |
| 8,652,145 B2 | 2/2014 | Maimon et al. |
| 8,679,404 B2 | 3/2014 | Liburd et al. |
| 8,869,982 B2 | 10/2014 | Hodshon et al. |
| 9,155,619 B2 | 10/2015 | Liu et al. |
| 9,523,189 B2 | 12/2016 | Tijssen |
| 10,130,466 B2 | 11/2018 | Campbell et al. |
| 2002/0120328 A1 | 8/2002 | Pathak et al. |
| 2003/0070944 A1 | 4/2003 | Nigam |
| 2005/0241981 A1 | 11/2005 | Gupta et al. |
| 2006/0155363 A1 | 7/2006 | LaDuca et al. |
| 2006/0195183 A1 | 8/2006 | Navia et al. |
| 2008/0082163 A1 | 4/2008 | Woo |
| 2008/0177381 A1 | 7/2008 | Navia et al. |
| 2009/0130162 A2 | 5/2009 | Pathak et al. |
| 2009/0164005 A1 | 6/2009 | Dove et al. |
| 2011/0147251 A1 | 6/2011 | Hodshon et al. |
| 2017/0056149 A1 | 3/2017 | Rajpara et al. |

OTHER PUBLICATIONS

O.W. Winston, D.H. Bates Saturated solutions for the control of humidity in biological research. Ecology 1960, 42:232-237.

M.E. Solomon, Control of humidity with potassium hydroxide, sulphuric acid, or other solutions. Bul. Entomol. Res 1951, 42:543-554.

E. L., Soderstrom, D. G. Brandl, and B. Mackey Responses of codling moth (*Lepidoptera:Tortricidae*) life stages to high carbon dioxide or low oxygen atmospheres. J. Econ. Entomol. 1990, 83:472-475.

J.V. Braun, and J.D. Braun. A simplified method of preparing solutions of glycerol and water for humidity control. Corrosion 1958 14(3):117-118.

Charles F. Forney, David G. Brandl Control of Humidity in Small Controlledenvironment Chambers using Glycerol-Water Solutions, HortTechnology 2.1 (1992): 52-54.

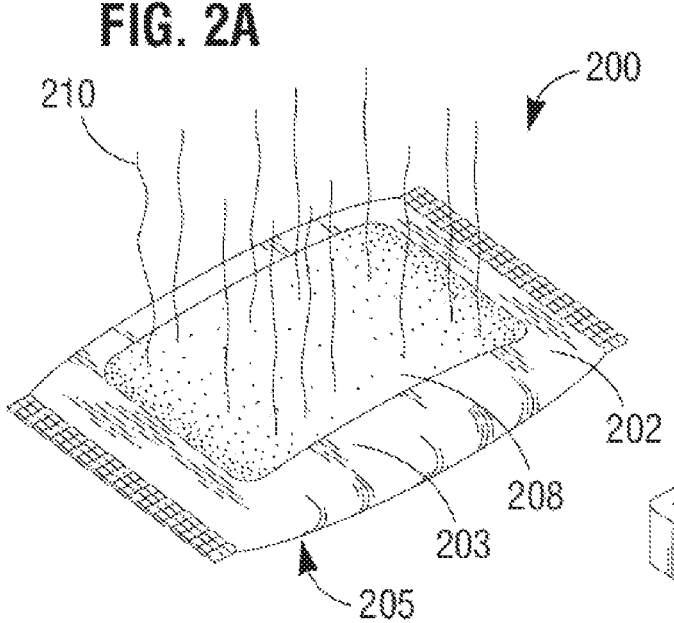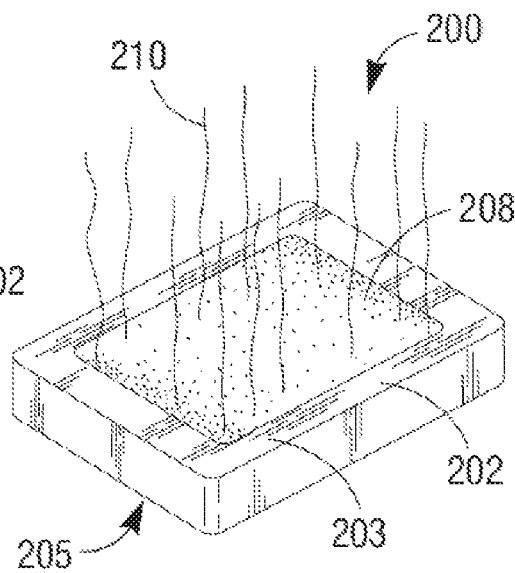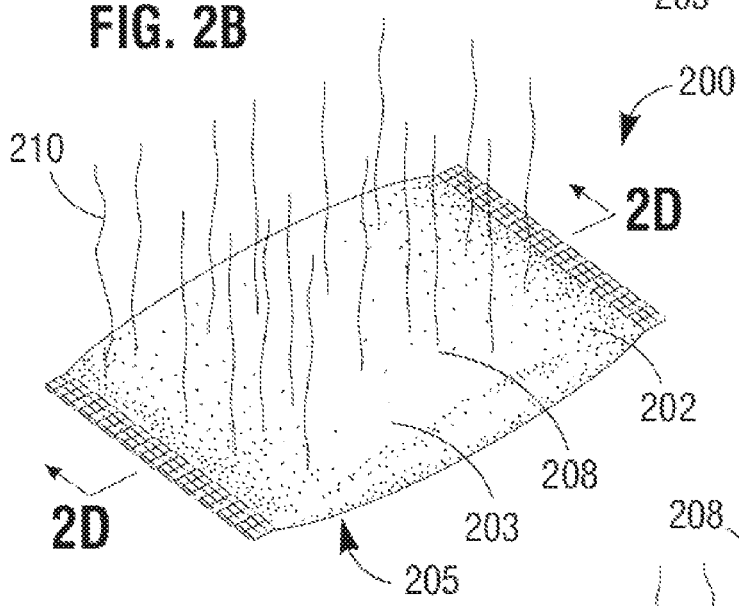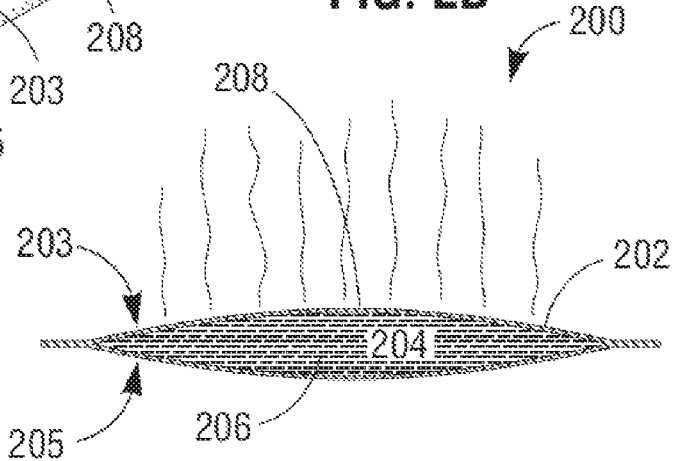

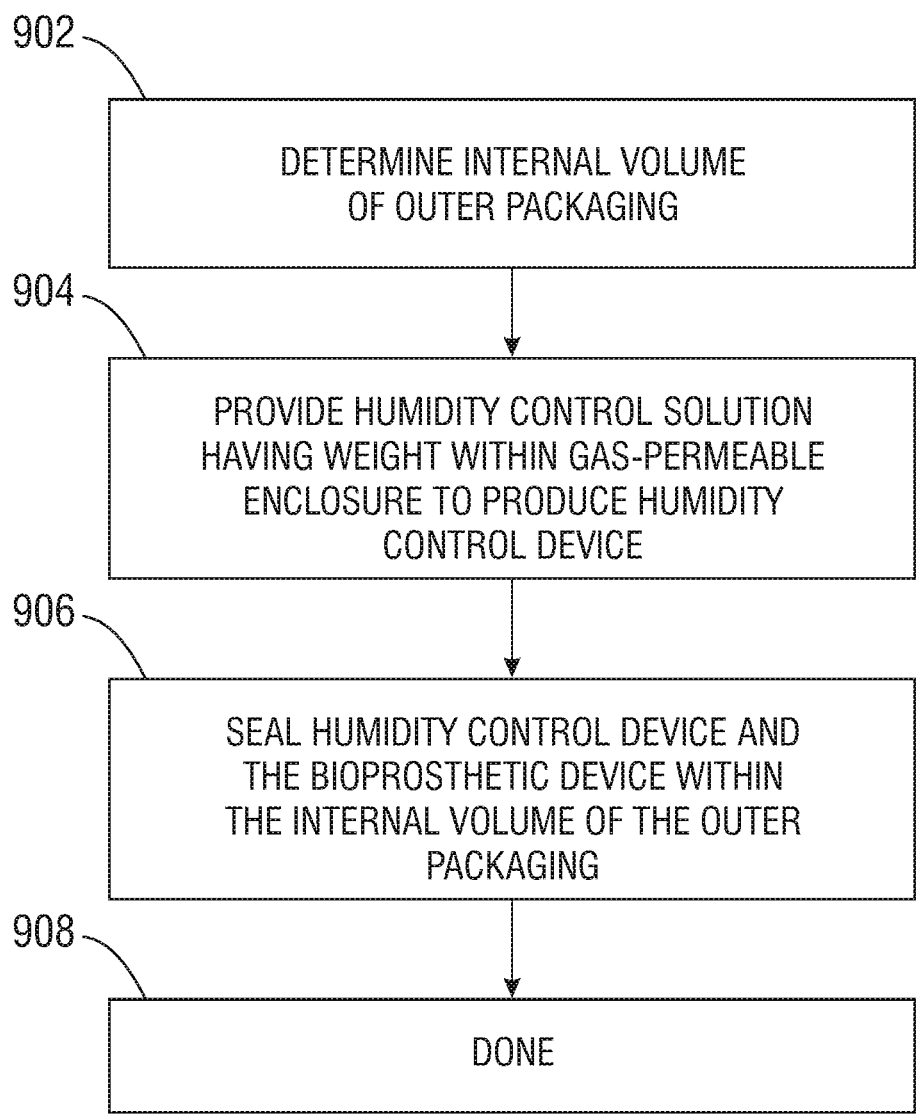

HUMIDITY-MANAGEMENT PACKAGING SYSTEMS AND METHODS

CROSS-REFERENCE TO RELATED APPLICATION

The present application is a continuation of U.S. patent application Ser. No. 15/909,111, filed Mar. 1, 2018, which claims priority to U.S. Provisional Patent Application No. 62/467,684, entitled "Humidity-Management Packaging System," filed Mar. 6, 2017, the entire contents of which are incorporated into this application by reference for all purposes.

TECHNICAL FIELD

This disclosure relates generally to packaging systems for storing bioprosthetic devices and, more particularly, to packaging systems that include a humidity control system configured to maintain a target relative humidity across a range of temperatures.

BACKGROUND

Bioprosthetic devices, and other medical and surgical components, can be moisture sensitive. A single medical device manufacturer may supply moisture-sensitive products across many different regions of the world as well as across seasons. The wide range of temperature and humidity across these regions and seasons place significant burdens on the optimization of the packaging system for these products. For example, a system that works well in North America may rapidly fail in Southeast Asia.

In the past, packaging systems for storing bioprosthetic devices have generally functioned merely as sterile packages. It would be desirable, however, to have packages with moisture management, such as a two-way moisture management system, which is able to function as both humidifier and dehumidifier by compensating for what would otherwise be changes to the relative humidity in the packaging. This could be done, for example, in response to temperature changes. It would also be desirable to have a moisture management system (e.g., a two-way moisture management system) for maintaining relative humidity under extreme conditions and during thermal shock events.

SUMMARY

This summary is meant to provide some examples and is not intended to be limiting of the scope of the invention in any way. For example, any feature included in an example of this summary is not required by the claims, unless the claims explicitly recite the features. Also, the features described can be combined in a variety of ways. The description herein relates to systems, assemblies, methods, devices, apparatuses, combinations, etc. that may be utilized for environment control in packaging. Various features and steps as described elsewhere in this disclosure can be included in the examples summarized here.

For example, various embodiments of packaging systems are described herein, which can be for storing a bioprosthetic device while maintaining a target relative humidity across a temperature range. The packaging system(s) can provide a moisture management system (e.g., a two-way moisture management system) that can adjust and control relative humidity, such as across a specified or desired range of relative humidity, within a degree of statistical confidence and reliability. The packaging system can be made from commercially available, medical-grade materials, and maintenance or replacement of the system may not be required.

In one embodiment, the packaging system includes a sealed package, which defines an internal space having an internal volume. The packaging system can optionally further include both the bioprosthetic device and a humidity control device within the internal space or volume of the package. The humidity control device can include a barrier, which defines an enclosed space. At least a portion of the barrier can include a gas-permeable membrane. A humidity control solution comprising glycerol can be provided in the enclosed space. The target relative humidity can be provided within the internal volume of the sealed package, and the humidity control device can maintain the target relative humidity across the temperature range by selectively liberating and absorbing water vapor. In one embodiment, the packaging system can maintain the target relative humidity within a tolerance of about ±10%. In one embodiment, the packaging system can maintain the target relative humidity within a tolerance of about ±5%.

In one embodiment, the bioprosthetic device can comprise a bioprosthetic tissue that has a reduced water content of about 25% (by weight) or less. In one embodiment, the bioprosthetic tissue can be glycerolized. In one embodiment, the bioprosthetic device can comprise a heart valve, and the bioprosthetic tissue can form leaflets of the heart valve.

In one embodiment, the gas-permeable membrane can have a water vapor transfer rate of about 0.02 to 0.07 grams per square inch (about 3-10 $mg/cm^2$) per 24 hours. In one embodiment, the gas-permeable membrane can have an average porosity of about 8 to 36 Gurley units. In one embodiment, the gas-permeable membrane can have a surface area, and a ratio of the surface area of the gas-permeable membrane to the internal volume of the sealed package can be from about 0.1 to about 0.5 $g/in^3$ (about 6-30 mg/mL). In some embodiments, the gas-permeable membrane can comprise or consist of a hydrophobic homopolymer. In some embodiments, the gas-permeable membrane can comprise or consist of a high-density polyethylene having a microfibrous structure. In some embodiments, the gas-permeable membrane can be a medical-grade material.

In some embodiments, the sealed package can include a polymer/foil pouch. In some embodiments, the sealed package can have a water vapor transfer rate of less than about 0.002 grams per day. In some embodiments, the sealed package can be hermetically sealed.

Each feature or concept outlined above is independent and can be combined with other features or concepts outlined above or with any other feature or concept disclosed in this application.

In one embodiment, the packaging system includes a sealed package, which has an internal space having an internal volume. The bioprosthetic device and a humidity control device can be provided within the internal space. The humidity control device can have a barrier, which defines an enclosed space that is in vapor communication with the sealed package. A humidity control solution comprising glycerol can be provided in the enclosed space. The humidity control solution can have a total weight of at least about 0.1 g per cubic inch (about 6 mg/mL) of the internal volume.

In one embodiment, the humidity control solution can maintain the target relative humidity across the temperature range by selectively liberating and absorbing water vapor. In one embodiment, the humidity control solution can further include an aqueous solution. In some embodiments, glycerol can be provided in a concentration of from about 34% to about 96% (by weight) of the humidity control solution and the aqueous solution can be provided in a concentration of from about 4% to about 66% (by weight) of the humidity control solution. In some embodiments, the concentration of the glycerol ($G_w$) in the humidity control solution can defined by the target relative humidity (RH) to be maintained within the internal volume of the sealed package according to Eq. 1.

$$G_w = 383(-0.189(RH)+19.9)^{0.0806} - 383 \quad \text{Eq. 1}$$

In one embodiment, the humidity control solution can further include a microbicidal agent. In a further optional embodiment, the microbicidal agent can be glutaraldehyde. In some embodiments, the glutaraldehyde can be provided in an amount of from about 0.3% to about 1%. In one embodiment, the aqueous solution may be about 97% (by volume) water and about 3% (by volume) of a solution of an about 0.625% (by weight) glutaraldehyde.

In some embodiments, the packaging system can maintain the target relative humidity across a temperature range of from about −18° C. to about 45° C. In some embodiments, the target relative humidity can be from about 15% to about 95%. In one embodiment, the packaging system can maintain the target relative humidity within a tolerance of about ±10%. In one embodiment, the packaging system can maintain the target relative humidity within a tolerance of about ±5%. In one embodiment, the target relative humidity (RH) to be maintained within the internal volume of the sealed package can be determined by the concentration of the glycerol ($G_w$) in the control solution according to Eq. 2.

$$RH = -\frac{\left(\frac{G_w + 383}{383}\right)^{12.4} - 19.9}{0.189} \quad \text{Eq. 2}$$

Each feature or concept outlined above is independent and can be combined with other features or concepts outlined above or with any other feature or concept disclosed in this application.

A method for storing a bioprosthetic device within a packaging system that maintains a target relative humidity across a temperature range is also provided. In one embodiment, the method includes determining an internal volume of an outer packaging, selecting the target relative humidity, providing a humidity control device comprising a humidity control solution disposed within a gas-permeable enclosure, and sealing the humidity control device and the bioprosthetic device within the internal volume of the outer packaging. In some embodiments, the humidity control solution can include glycerol.

In one embodiment, the method can further include selecting a target relative humidity from about 15% to about 95%. In one embodiment, the method can maintain the target relative humidity within the packaging system within a tolerance of about ±10%. In one embodiment, the method can maintain the target relative humidity within the packaging system within a tolerance of about ±5%. In one embodiment, the target relative humidity (RH) to be maintained within the internal volume of the outer packaging can be determined by the concentration of the glycerol ($G_w$) in the humidity control solution according to Eq. 2.

$$RH = -\frac{\left(\frac{G_w + 383}{383}\right)^{12.4} - 19.9}{0.189} \quad \text{Eq. 2}$$

In one embodiment, a concentration of glycerol ($G_w$) (by weight) in the humidity control solution can be defined by the target relative humidity (RH) to be maintained within the internal volume of the outer packaging according to Eq. 1.

$$G_w = 383(-0.189(RH)+19.9)^{0.0806} - 383 \quad \text{Eq. 1}$$

In one embodiment, the weight of the humidity control solution provided can be at least about 0.1 g per cubic inch (about 6 mg/mL) of the internal volume. In one embodiment, the method can maintain the target relative humidity across the temperature range from about −18° C. to about 45° C. In one embodiment, the gas-permeable enclosure can have a water vapor transfer rate of from about 0.02 to about 0.07 grams per square inch (about 3-10 mg/cm$^2$) per 24 hours. In one embodiment, the method can further include subjecting the outer packaging to a terminal sterilization process.

Each feature or concept outlined above is independent and can be combined with other features or concepts outlined above or with any other feature or concept disclosed in this application. Other features and advantages of the invention should become apparent from the following description of the preferred embodiments, taken in conjunction with the accompanying drawings, which illustrate, by way of example, the principles of the invention.

BRIEF DESCRIPTION OF THE DRAWINGS

FIGS. 2A-2C are perspective views of exemplary embodiments of humidity control devices.

FIG. 2D is a side cross-sectional view of an exemplary humidity control device.

FIG. 9 illustrates an exemplary method of storing a bioprosthetic device within a packaging system.

DETAILED DESCRIPTION OF CERTAIN EMBODIMENTS

Figure 1A:
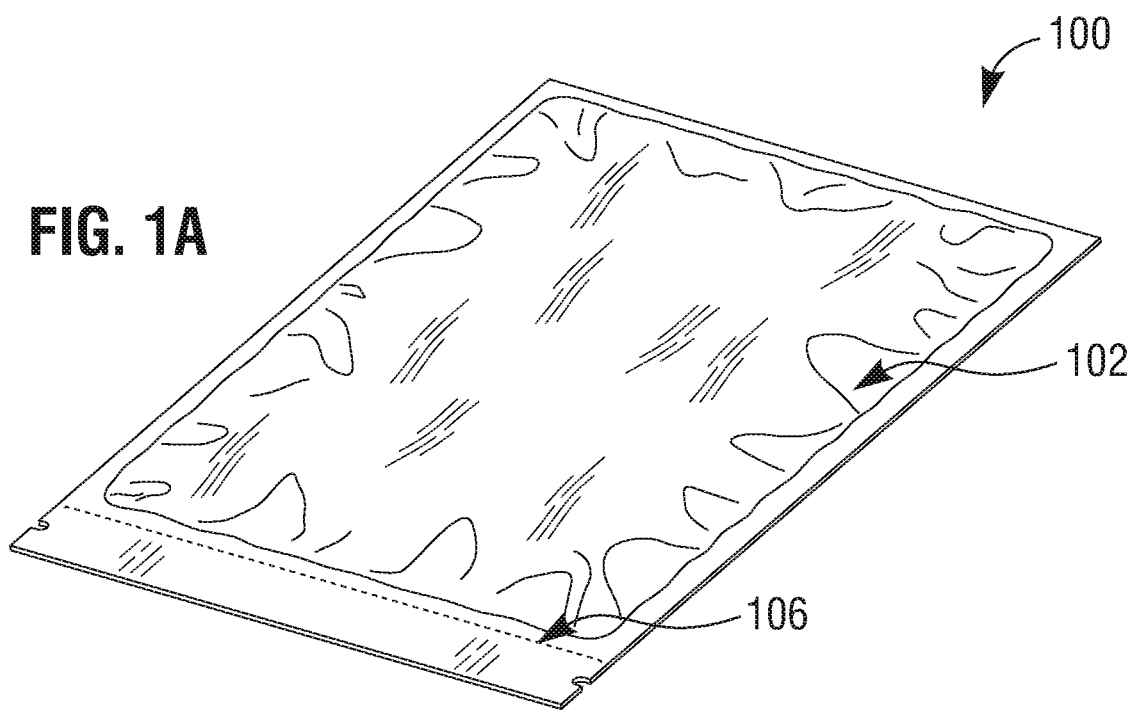
FIGS. 1A and 1B are perspective views of an exemplary outer packaging.
Figure 3:
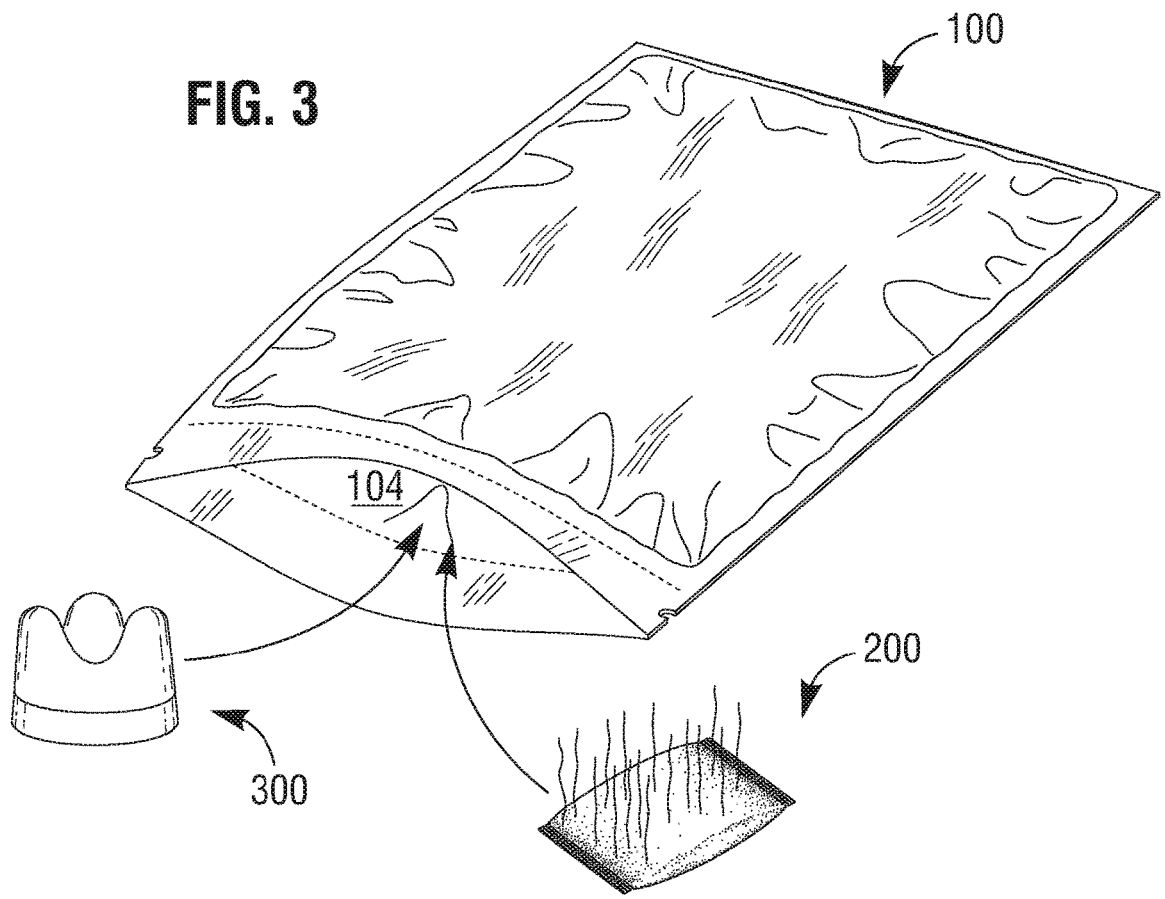
FIG. 3 is a perspective view of an exemplary packaging system.
Figure 4:
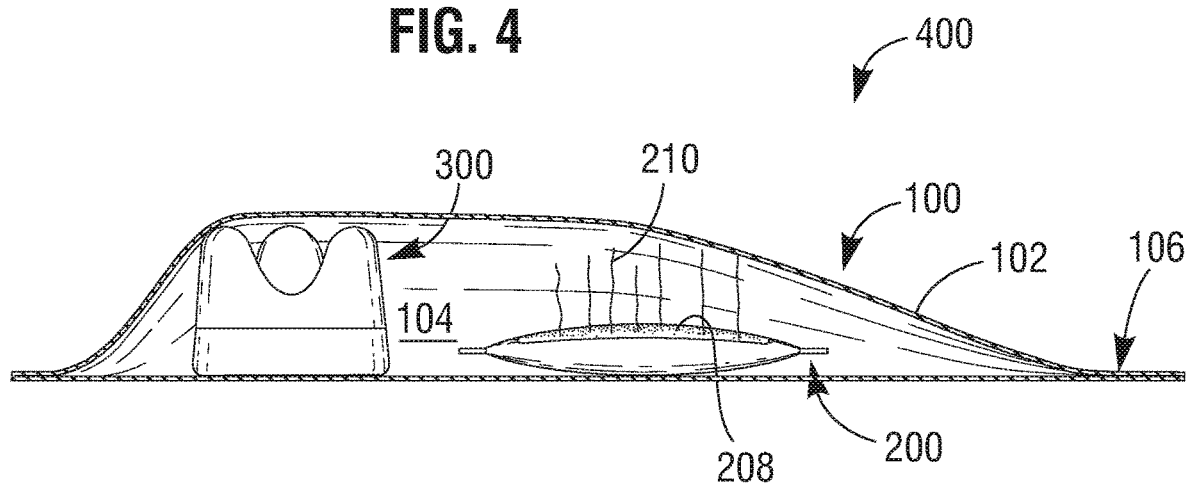
FIG. 4 is a side cross-sectional view of an exemplary packaging system.

With reference now to FIG. 1A through FIG. 4 of the illustrative drawings, there are shown exemplary packaging systems (e.g., packaging system 400 in FIG. 4) and exemplary elements thereof for storing a bioprosthetic device (e.g., exemplary bioprosthetic device 300 in FIGS. 3 and 4). The packaging systems generally include an outer packaging 100 that defines an internal space 104 (FIGS. 1A and 1B). The systems generally include one or multiple bioprosthetic devices and one or multiple humidity control devices (e.g., exemplary humidity control devices 200 in FIGS. 2A-2D), which are preferably stored within the internal space of the outer packaging.

As will be described below, the packaging system is generally configured to maintain a target relative humidity within the internal space across a range of temperatures. As used herein, each of the terms "target relative humidity" and "desired relative humidity" can refer to a particular relative humidity value or a range of relative humidities that includes the particular value, as will be apparent according to the context. When the packaging system is exposed to higher ambient temperatures, relative humidity within the internal space will tend to decrease and the humidity control device will release water vapor or moisture vapor 210 to restore the relative humidity within the internal space to the target relative humidity. When the packaging system is exposed to lower ambient temperatures, relative humidity within the internal space will tend to increase and the humidity control device will absorb water vapor to restore the relative humidity within the internal space to the target relative humidity.

Bioprosthetic Devices

The bioprosthetic device(s) that may be stored using the system and method described herein can encompass a variety of different devices. Examples of such bioprosthetic devices include replacement heart valves, aortic conduits, catheters, stents, grafts, stent-grafts, vascular stents, vascular grafts, patches, bone grafts, and tissue grafts to name just a few.

The bioprosthetic device(s) can include bioprosthetic tissue or other biological materials. Bioprosthetic tissue incorporated in the bioprosthetic devices can be a biological tissue, or any connective or collagenous tissue, whether directly or derived from animal or human sources, and whether in its native form, or modified chemically or otherwise. The bioprosthetic tissue can include, for example, all or a portion of at least one of native cardiac valves, blood vessels, skin, hides, epidermis, dura mater, pericardium, small intestinal submucosa, ligaments, and tendons. The bioprosthetic tissue can be pericardium from animal sources, including but not limited to bovine, porcine, kangaroo, bison, and equine pericardium. The bioprosthetic tissue can also be selected based on certain desired characteristics of the tissue, such as the orientation of collagen fibers. For example, kangaroo hides are believed to have collagen fibers that are aligned substantially parallel to one another. The bioprosthetic tissue can further be any engineered tissue that is formed using a natural or biodegradable synthetic scaffold that can be seeded with cells from humans (autologous or allogenic) or from animal sources.

Embodiments of the system are also suitable for packaging, storing, and/or shipping any device or object for which moisture or humidity control is desired, for example, medical devices, electronics, semiconductors, batteries, magnetic media, optics, documents, alloys, jewelry, chemicals, pharmaceuticals, biologics, or the like.

Fixation Process

Some embodiments of the bioprosthetic tissue may be subjected to a fixation process which preferably renders the bioprosthetic tissue less antigenic and at least partially, if not completely, cross-linked. The fixation process is understood to include any chemical, thermal, or other processes, the result of which the bioprosthetic tissue is preserved and rendered more mechanically and dimensionally stable than if the tissue had not been subjected to the fixation process.

The fixation process can include contacting the tissue with one or more fixatives or cross-linking agents. Known fixatives or cross-linking agents include aldehydes, dialdehydes, polyaldehydes, amines, diamines (such as 1,6-hexanediamine and 1,7-heptanediamine), polyamines, diisocyanates, carbodiimides, photooxidation agents, and polyepoxide compounds. In one embodiment, the fixative is an aldehyde, such as formaldehyde or glutaraldehyde.

Glutaraldehyde-fixed tissue is particularly vulnerable to calcification because glutaraldehyde fixation generates residual aldehyde groups and labile Schiff bases. The residual aldehydes and Schiff bases are believed to be potential binding sites for calcium. Moreover, free aldehyde groups may oxidize to carboxylic acid groups, which are known to attract and bind calcium. Various techniques have therefore been developed to reduce the aldehyde and/or acid levels of glutaraldehyde-fixed tissues, and therefore its propensity to calcify after implantation in a host.

One technique for reducing aldehyde and/or acid levels in glutaraldehyde-fixed tissue is to include a heat-treating step during or after the bioprosthetic tissue is contacted or treated with glutaraldehyde. In one embodiment, the bioprosthetic tissue can be heat treated any time prior to implantation in a host by heating in a saline or physiologic solution either before or after fixation with glutaraldehyde. In another embodiment, the bioprosthetic tissue can be heat treated in a glutaraldehyde solution, either during or after the initial fixation of the tissue using glutaraldehyde. The heat treatment can be performed by immersing the tissue in the selected saline, physiologic, and/or fixative solution, and heating the solution to a temperature of from about 25° C. to about 80° C. or from about 35° C. to about 55° C. The solution can be heated either before or after the bioprosthetic tissue is added to the solution. The tissue can be heat treated for from a few seconds to several months, or from about 4 weeks to about 22 weeks. In one embodiment, the tissue is be heated in a glutaraldehyde solution at a temperature of from about 60° C. to about 70° C. for a duration of from about 1 day to about 7 days. In one embodiment, the tissue is heated in a glutaraldehyde solution at a temperature of about 65° C. for about 3-5 days or for about 4 days.

Embodiments of glutaraldehyde-fixed tissue demonstrate reduced aldehyde and carboxylic acid contents after heat treatment, and thus a marked reduction in calcification after implantation, as compared with glutaraldehyde-fixed tissue without heat treatment. Heat treatment of glutaraldehyde-fixed tissue is described, for example, in U.S. Pat. No. 6,561,970, issued May 13, 2003 to Edwards Lifesciences, the entire contents of which is incorporated herein by reference.

The fixation process can also further include pre-conditioning, pre-stressing, or pre-damaging fixed, bioprosthetic tissue to generate additional calcium binding sites, which can subsequently be capped, as described in U.S. Patent Application Publication No. 2008/0302372 A1, published Dec. 11, 2008, entitled "Methods for Pre-Stressing and Capping Bioprosthetic Tissue" to Edwards Lifesciences, the entire contents of which are incorporated herein by reference. In one embodiment, the bioprosthetic tissue can be subjected to a rapid pulsed fluid flow (for example, from about 4 Hz to about 1,500 Hz), repeatedly flexed, exposed to elevated temperature (for example, from about 26° C. to about 65° C.), contacted with an acidic solution (for example, pH in the range of from about 4 to about 7), contacted with an alkaline solution (for example, pH in the range of from about 8 to about 10), or any combination of the foregoing for the purpose of generating additional calcium binding sites, which can be capped and/or reduced in a separate treatment process.

Treatment with Capping and/or Reducing Agents

Embodiments of the bioprosthetic tissue can include functional groups that predispose the tissue to calcification, which can include any combination of those that exist natively in the bioprosthetic tissue, that are generated under cross-linking or fixation, or that result from any number of chemical or physical processes, including the pre-conditioning, pre-stressing, and/or pre-damaging disclosed herein.

For example, it is believed that many negatively charged carboxylic acid groups are formed after glutaraldehyde fixation of bioprosthetic tissue, and these groups attract and bind calcium ions due to their negative charges and electrostatic interactions with positively charged ions, leading to calcification of the tissue or other adverse cellular interactions.

Accordingly, embodiments of the bioprosthetic tissue can be treated with a capping agent. The capping agent can be any agent that can block, remove, or alter a functional group that can actually or potentially produce an undesirable interaction between the bioprosthetic tissue and the host, such as calcification, immunological reaction, pannus formation, and the like.

In one embodiment, the bioprosthetic tissue can be treated with the capping agent without a step of fixing or crosslinking the bioprosthetic tissue. In one embodiment, the bioprosthetic tissue can be treated with the capping agent before or after the step of fixing or crosslinking the bioprosthetic tissue.

In one embodiment, the capping agent can be one or a combination of the following: amines, including alkyl amines, amino alcohols, including ethanolamine, amino acids (including lysine and hydroxylysine), amino sulfonates (including taurine, amino sulfates, dextran sulfate, and chondroitin sulfate), a hydrophilic multifunctional polymer (including polyvinyl alcohol and polyethyleneimine), a hydrophobic multifunctional polymer, an α-dicarbonyl (including methylglyoxyl, 3-deoxyglucosone, and glyoxal), a hydrazide (including adipic hydrazide), an N,N-disuccinimidyl carbonate, a carbodiimide (including 1-ethyl-3-[3-dimethylaminopropyl]carbodiimide hydrochloride (EDC), N-cyclohexyl-N'-(2-morpholinoethyl) carbodiimide (CMC), 1,3-dicyclohexyl carbodiimide (DCC), and 2-chloro-1-methylpyridinium iodide (CMPI)), an antibiotic, a cell recruiting agent, a hemocompatibility agent, an anti-inflammatory agent, an anti-proliferative agent, an immunogenic suppressing agent, a reducing agent (including sodium cyanoborohydride, sodium borohydride, sodium bisulfite in acetylacetone, and formic acid in formaldehyde), and a mono-, di- or polyepoxy alkane.

In one embodiment, the capping agent can be any agent that is reactive with a functional group, wherein the functional group is a free aldehyde or a free carboxylic acid. The capping agent can be an amine, such as an alkyl amine or an amino alcohol. The capping agent can be an ethanolamine, for example, ethanolamine.

Regardless, certain reactions of the capping agent and functional groups may produce labile Schiff bases, and it may be desirable to reduce the Schiff bases, thereby converting them into more stable amines.

Accordingly, some embodiment of the treatment of the bioprosthetic tissue can further include treatment with a reducing agent. The reducing agent can be selected to reduce Schiff bases formed from the reaction of the crosslinking agent and the bioprosthetic tissue, the capping agent and the bioprosthetic tissue, and/or the capping agent and the crosslinking agent. In one embodiment, the bioprosthetic tissue can be treated with the reducing agent, with or without fixing or crosslinking the bioprosthetic tissue. In another embodiment, the bioprosthetic tissue can be treated with the reducing agent, with or without the capping agent. In a further embodiment, the bioprosthetic tissue can be treated with the reducing agent, with or without both fixing or crosslinking, and capping the bioprosthetic tissue.

The reducing agent can be any one or a combination of reducing agents, for example, reducing agents that comprise a borohydride. In one embodiment, the reducing agent can be one or a combination selected from the group consisting of sodium borohydride, sodium cyanoborohydride, sodium triacetoxyborohydride, alkyl borohydride, amino borohydride, lithium aminoborohydrides, and an organoborate hydride salt having the formula $XBR_3H$, where each R is an independently selected alkyl group and X is lithium, sodium, or potassium. The lithium aminoborohydride can be a lithium dimethylaminoborohydride, a lithium morpholinoborohydride, and a lithium pyrrolidinoborohydride, or the corresponding sodium or potassium salts, to name a few. The organoborate hydride salt reducing agent can be a lithium tri-sec-butyl(hydrido)borate, a sodium tri-sec-butyl(hydrido)borate, or a potassium tri-sec-butyl(hydrido)borate. The reactivity of aminoborohydrides in general, can be tailored by modifying the amine group and/or the cation (lithium>sodium>potassium). In some embodiments, the reducing agent comprises sodium bisulfate in acetylacetone and/or formic acid in formaldehyde.

The bioprosthetic tissue can be subjected to a treating step in which it is treated with a capping agent and a reducing agent in a solution. In one embodiment, the capping agent is selected to react with one or more functional groups associated with the bioprosthetic tissue and the reducing agent is selected to reduce Schiff bases. The Schiff bases can be formed from any one or more of the reaction of the crosslinking agent and the bioprosthetic tissue, the reaction of the capping agent and the bioprosthetic tissue, and the reaction of the capping agent and the crosslinking agent. The capping agent can be an amine or an amino alcohol, such as an ethanolamine, the functional groups can be an aldehyde or a carboxylic acid, the reducing agent can be a borohydride, such as a sodium borohydride and the crosslinking agent can be an aldehyde-containing agent, such as glutaraldehyde. The treating can be performed sequentially with a first step of contacting the tissue with a solution of the capping agent and a second step of contacting the tissue with a solution of the reducing agent, or simultaneously with both the capping and reducing agents present in the solution. In one embodiment, the treating can be performed with the capping agent and reducing agent in a solution on an orbital shaker operating at from about 80 to about 100 rpm for about 4 hours.

Exemplary methods for treating bioprosthetic tissue with capping and reducing agents are described, for example, in U.S. Pat. No. 7,972,376, issued Jul. 5, 2011 to Edwards Lifesciences Corp., the entire contents of which are incorporated by reference as if fully set forth herein.

Dry Storage

The bioprosthetic tissue can be treated such that it does not require storage in a liquid, such as a preservative solution. Examples of such preservative solutions include glutaraldehyde, formaldehyde, and saline solutions. The dry storage of bioprosthetic devices has certain advantages, including reduced storage requirements and ease of handling. Because preservative solutions often include toxic and/or carcinogenic chemicals, implantable medical devices stored in preservative solutions often require extensive rinsing prior to implantation. Eliminating the use of such preservative solutions therefore obviates the need for extensive rinsing and therefore permits for greater efficiency in the operating room prior to implantation, as well as reduced exposure of personnel to a potentially hazardous preservative solution.

As used herein, "dry storage" is understood to mean that the bioprosthetic device is not partially or completely immersed in a liquid preservative solution for storage. For example, "dry storage" can refer to the environment in which the implantable bioprosthetic device is stored when it is packaged for transit after manufacture. "Dry storage" does not, however, preclude the step of hydrating the implantable medical device once the package is opened or just prior to implantation. "Dry storage" also does not preclude the presence of residual moisture or water that may be present in the bioprosthetic tissue or humidity in the packaging system.

In one embodiment, the bioprosthetic tissue can undergo treatment with anhydrous, non-aqueous, or aqueous solutions to partially or substantially, if not completely, dehydrate the bioprosthetic tissue for dry storage. The bioprosthetic tissue following treatment can contain residual water or moisture within the tissue interstices but can be packaged for dry storage.

Glycerol Treatment

The bioprosthetic tissue can further undergo treatment with anhydrous, non-aqueous, or aqueous solutions to at least partially, substantially, or completely, dehydrate the bioprosthetic tissue for dry storage, as described above. It is understood that the bioprosthetic tissue can retain an amount of water within its interstices and/or bound to the tissue, for example, to collagen. Embodiments of bioprosthetic tissue suitable for dry storage include water bound to the tissue itself, with substantially all interstitial water removed.

In one embodiment, the solution comprises glycerol and, preferably, a solution comprising about 75 wt % glycerol and about 25 wt % ethanol. In one embodiment, the solution is non-aqueous, that is, a solution in which the solvent is not water. In one embodiment, the solution can be anhydrous. The bioprosthetic tissue can be contacted with, for example, immersed in, the glycerol solution for a time sufficient to penetrate through the tissue and displace a substantial amount of water in the tissue interstices. In one embodiment, the bioprosthetic tissue can be contacted with the glycerol solution for about 4 or more hours. The glycerolized bioprosthetic tissue can then be removed from the solution and excess solution removed, for example, on standing in a clean hood.

In another embodiment, a solution of glycerol and a $C_1$-$C_3$ alcohol can be anhydrous or non-aqueous, wherein the treatment solution comprises about 60-95% by volume glycerol. It is understood that an anhydrous solution does not contain water, whereas a non-aqueous solution may contain water. Suitable treatment for the biological tissues are described in U.S. Pat. No. 8,007,992, issued Aug. 30, 2011, to Edwards Lifesciences Corp., the entire contents of which are incorporated herein by reference as if fully set forth herein.

In yet a further embodiment, an aqueous glycerol solution can be used to at least partially dehydrate and to glycerolize the tissue, as described in U.S. Pat. No. 6,534,004, issued Mar. 18, 2003, issued to The Cleveland Clinic Foundation, the entire contents of which are incorporated herein by reference in its entirety as if fully set forth herein.

In one embodiment, one or more antioxidants can be added to the glycerol treatment solution, which is believed to reduce or prevent oxidation of the bioprosthetic tissue during subsequent sterilization and storage of the tissue.

In one embodiment, the bioprosthetic tissue can be treated with an anhydrous, non-aqueous, or aqueous solution that comprises glycerol. In one embodiment, the anhydrous, non-aqueous, or aqueous solution can comprise glycerol at about 25% by volume, about 30% by volume, about 35% by volume, about 40% by volume, about 45% by volume, about 50% by volume, about 55% by volume, about 60% by volume, about 65% by volume, about 70% by volume, about 75% by volume, about 80% by volume, about 85% by volume, about 90% by volume, or about 95% by volume. In one embodiment, the anhydrous, non-aqueous, or aqueous solution comprises an amount of glycerol within and including any two of the foregoing values.

In one embodiment, the anhydrous, non-aqueous, or aqueous glycerol solution can comprise alcohol. In one embodiment, the anhydrous, non-aqueous, or aqueous solution can comprise alcohol at about 5% by volume, about 10% by volume, about 15% by volume, about 20% by volume, about 25% by volume, about 30% by volume, about 35% by volume, about 40% by volume, about 45% by volume, about 50% by volume, about 55% by volume, about 60% by volume, about 65% by volume, about 70% by volume, or about 75% by volume. In one embodiment, the anhydrous, non-aqueous, or aqueous solution comprises an amount of alcohol within and including any two of the foregoing values. The alcohol can be any one or a combination of $C_1$, $C_2$, $C_3$, $C_4$, and $C_5$ alcohols, such as ethanol, propanol, and butanol.

The bioprosthetic tissue can also be treated by means other than the glycerol treatment process described above to dry or dehydrate the bioprosthetic tissue. The terms "dry" or "dehydrate," as used herein with reference to the bioprosthetic tissue or the bioprosthetic device, is understood to include embodiments that include residual water or moisture that may be present in the bioprosthetic tissue following glycerol or other treatment to reduce the water content of the bioprosthetic tissue. In one embodiment, the water content of the dried or dehydrated bioprosthetic tissue following glycerol or other treatment is about 25% by weight or less, about 20% by weight or less, about 15% by weight or less, about 10% by weight or less, about 9% by weight or less, about 8% by weight or less, about 7% by weight or less, about 6% by weight or less, about 5% by weight or less, about 4% by weight or less, about 3% by weight or less, about 2% by weight or less, or about 1% by weight or less. The percentages provided herein are understood to be based on the combined weight of the bioprosthetic tissue and water content.

Packaging System

Figure 1B:
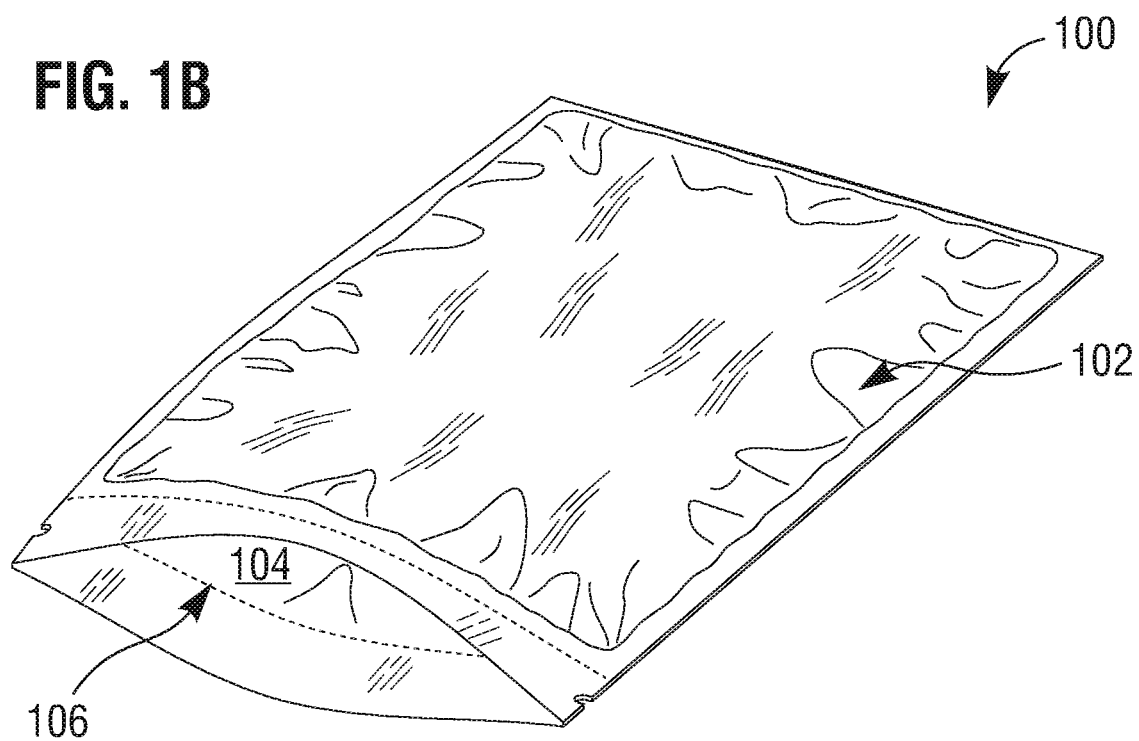

With reference now to FIGS. 1A and 1B, in one embodiment, the packaging system includes an outer packaging 100, which can be a sealable pouch, tray, and/or clamshell, which can comprise, for example, foil, polymer, or a combination thereof. When sealed, the outer packaging 100 provides an internal space 104 for storing one or multiple bioprosthetic devices in a relatively sterile environment. The outer packaging 100 can be a rectangular pouch, as show in FIGS. 1A and 1B, or any other shape or configuration suitable for storing the bioprosthetic device and a humidity control device 200 in a relatively sealed environment. In addition, the outer packaging 100 can be formed from a polymer/foil pouch or any other packaging material 102 that is impermeable to microorganisms and that has a low water or moisture vapor transfer rate. The outer packaging's low water vapor transfer rate can mitigate the effect of ambient moisture on the relative humidity within the internal space 104 of the sealed outer packaging 100. In one embodiment, the outer packaging 100 preferably has a water vapor transfer rate of less than about 2 milligrams per day per package.

As shown in FIG. 3, at least one bioprosthetic device 300 and at least one humidity control device 200 can be placed within the internal space 104 of the outer packaging 100 for storage. Thereafter, the outer packaging 100 can be closed and sealed, whereupon the sealed outer package 100 provides an internal space 104 can be inaccessible to microorganisms and relatively unaffected by ambient relative humidity.

With reference to FIGS. 2A through 2D, illustrative embodiments of the humidity control device 200 are shown. While these illustrations depict the humidity control device 200 to have a generally pouch-like or box-like shape, the overall shape of the humidity control device is not critical. For example, the humidity control device 200 can be generally pouch-like, as illustrated by FIGS. 2A, 2B, and 2D, box-like as illustrated by FIG. 2C, spherical, cylindrical, or any other suitable shape. In some embodiments, the humidity control device 200 is at least partially integrated with the outer packaging, for example, disposed in at least one well in a tray or clamshell, or sharing at least one wall or surface with a pouch, lid, or cover.

The humidity control device 200 preferably includes a barrier 202 that defines an enclosed space 204. In one embodiment, the barrier 202 is formed from a first portion 203 and a second portion 205, which are sealed at their periphery to define the enclosed space 204 therebetween.

At least a portion of the barrier 202 preferably includes a gas-permeable membrane 208. For example, with reference to FIG. 2A, in one embodiment, the first portion includes the gas-permeable membrane 208 and the second portion 205 comprises a non-permeable material, such as about 100 gauge (about 25 μm) biaxially-oriented film made of polyamide resin (BOPA or Biax Nylon), although other thicknesses, materials, and/or polymers are used in other embodiments. For example, some embodiments of the second portion are sufficiently rigid to maintain a desired shape under the expected conditions of use. In one embodiment, shown in FIG. 2B, both the first portion and the second portion 205 comprise the gas-permeable membrane. In one embodiment, the gas-permeable membrane is a medical-grade material. In one embodiment, the gas-permeable membrane comprises a hydrophobic homopolymer. In one embodiment, the gas-permeable membrane comprises a high-density polyethylene having a microfibrous structure.

The gas-permeable membrane 208 can facilitate the two-way transfer of water vapor between the enclosed space 204 of the humidity control device 200 and the internal space 104 of the outer packaging 100. The back-and-forth movement of water vapor 210 between these volumes or spaces establishes a relative humidity equilibrium that tends to maintain a desired target relative humidity range in the enclosed space 204. To reduce, minimize, or avoid damage to the bioprosthetic device, it is preferable to reestablish the target relative humidity range in a packaging system relatively quickly. In general, the higher the gas-permeable membrane's water vapor transfer rate, the better the performance in retaining the target relative humidity range within the enclosed space. However, undesirable seeping can occur if the water vapor transfer rate exceeds about 0.07 grams per square inch (about 10 mg/cm$^2$) per 24 hours. Therefore, in one embodiment, the gas-permeable membrane 208 can have a water vapor transfer rate of from about 0.02 to about 0.07 grams per square inch (about 3-10 mg/cm$^2$) per 24 hours. In one embodiment, the gas-permeable membrane 208 can have a water vapor transfer rate of from about 0.03 to 0.05 grams per square inch (about 5-8 mg/cm$^2$) per 24 hours. In one embodiment, the gas-permeable membrane 208 may have a water vapor transfer rate of about 0.03 grams per square inch (about 5 mg/cm$^2$) per 24 hours. In one embodiment, the gas-permeable membrane 208 may have an average porosity of from about 8 to about 36 Gurley units (ISO 5636-5:2003).

With reference to FIG. 4, a side sectional view is shown of an exemplary embodiment of the packaging system 400 for storing a bioprosthetic device 300. This embodiment includes a sealed package 100 that defines an internal space 104 having an internal volume. The bioprosthetic device(s) and a humidity control device(s) 200 are preferably stored within the sealed package's internal space. In one embodiment, the humidity control device 200 includes a barrier that defines an enclosed space and a humidity control solution in the enclosed space 104. A portion of the barrier can include a gas-permeable membrane. A target relative humidity range is provided within the internal volume of the sealed package with the control solution preferably maintaining the target relative humidity range across a temperature range by selectively liberating and absorbing water vapor. In one embodiment, as shown, the bioprosthetic device is unprotected within the sealed package. In one embodiment, the bioprosthetic device is stored within internal packaging, for example, a polyethylene terephthalate (PETG) tray with a breathable lid (not shown) before being placed within the internal space of the sealed package. In some embodiments, the bioprosthetic device is coupled to an accessory, for example, at least a portion of a holder or delivery device, for example.

It should be understood that the internal volume of the outer packaging's internal space will inform the configuration of the gas-permeable membrane. For example, to maintain adequate performance and restore relative humidity to the target relative humidity range within a desired time interval, the surface area of the gas-permeable membrane may be larger for larger internal volumes. In one embodiment, a ratio of the surface area of the gas-permeable membrane to the internal volume of the sealed package is from about 0.1 to about 0.5 g/in$^3$ (about 6-30 mg/mL). Some embodiments include a plurality of humidity control devices to provide the desired performance and/or dimensional characteristics.

With reference now to FIG. 2D, a humidity control solution 206 is disposed within the barrier 202. In some embodiments, the humidity control solution 206 comprises glycerol, which is a polyol compound with three hydroxyl groups and a high affinity for water. Glycerol solutions will absorb or release moisture until a concentration is reached that is in equilibrium with the relative humidity of the packaging system.

For example, an aqueous solution of 80 grams of glycerol and 20 grams of water will have an equilibrium relative humidity of about 50%, at 24° C., within a closed system. Increasing the ambient temperature from 24° C. to 45° C. would normally decrease the relative humidity within the system, but water will evaporate from the glycerol solution to bring the relative humidity back to about 50%. On the other hand, if the ambient temperature changes from 24° C. to 1° C., relative humidity will normally increase, but the glycerol solution will absorb water to bring relative humidity back to about 50%.

The relationship between glycerol concentration, measured as specific gravity (SG), and an equilibrium relative humidity (RH) that forms in a closed system at 24° C. is described by Eq. 3.

$$RH = -\frac{SG^{12.4} - 19.9}{0.189} \qquad \text{Eq. 3}$$

To aid in the determination of a solution needed to produce a given equilibrium relative humidity, the above formula can be rearranged for specific gravity. Thus, the specific gravity of a glycerol solution needed to produce a desired equilibrium relative humidity is defined by Eq. 4.

$$SG = (-0.189RH + 19.9)^{0.0806} \qquad \text{Eq. 4}$$

A ratio of water and glycerol that provides a desired specific gravity can be calculated by Eq. 5, in which $G_w$ is the percent glycerol (by weight) in the solution:

$$G_w = 383 SG - 383 \qquad \text{Eq. 5}$$

The volume of glycerol needed to prepare the solutions can be calculated according to Eq. 6, in which $G_v$ is the volume of glycerol in milliliters, $W_t$ is the total weight or mass of the solution in grams, and 1.2262 is the density of pure glycerol in grams per milliliter, at 24° C.:

$$G_v = \frac{G_w W_t}{100 \times 1.262} \qquad \text{Eq. 6}$$

Finally, the volume of water needed to prepare the solutions can be calculated according to Eq. 7, in which $H_v$ is the volume of water in milliliters and 1 is the density of water, in grams per milliliter:

$$H_v = \frac{100 - G_v}{100 \times 1} \qquad \text{Eq. 7}$$

In an optional embodiment, a microbicidal agent such as glutaraldehyde can be added to the volume of water to maintain proper log reduction of microbial activity within the humidity control device, for example, to a sterility assurance level (SAL) of $10^{-6}$. In a preferred embodiment, the humidity control solution comprises glycerol and an aqueous solution that contains about 97% (by volume) water and about 3% (by volume) of an about 0.625% (by weight) aqueous glutaraldehyde solution.

Using the above equations, various humidity control solutions of glycerol, water, and glutaraldehyde can be used to maintain virtually any desired relative humidity. Table I below provides examples of target relative humidity levels and some potential configurations of the associated humidity control solution, where "RH" is the target relative humidity, "SG" is the specific gravity of the humidity control solution, "$G_w$" is the percent glycerol (by weight) in the humidity control solution, "Wt" is the total weight or mass of the humidity control solution in grams, $G_v$ is the volume of glycerol in milliliters in the humidity control solution, "$H_v$" is the volume of water in milliliters in the humidity control solution, "GL" is the volume in milliliters of an aqueous solution that is 97% (by volume) water and 3% (by volume) of a 0.625% (by weight) aqueous glutaraldehyde solution, and "Glutaraldehyde" is the volume of glutaraldehyde in milliliters contained in the solution of the "$G_L$" column.

TABLE I

| RH (%) | SG | $G_w$ (%) | Wt (g) | $G_v$ (mL) | $H_v$ (mL) | $G_L$ (mL) | Glutaraldehyde (mL) |
|---|---|---|---|---|---|---|---|
| 15 | 1.257 | 98.4 | 8  | 6.24  | 0.13 | 0.13 | 0.00 |
|    |       |      | 16 | 12.48 | 0.26 | 0.26 | 0.01 |
|    |       |      | 24 | 18.71 | 0.38 | 0.40 | 0.01 |
| 20 | 1.251 | 96.2 | 8  | 6.10  | 0.30 | 0.31 | 0.01 |
|    |       |      | 16 | 12.20 | 0.61 | 0.63 | 0.02 |
|    |       |      | 24 | 18.29 | 0.91 | 0.94 | 0.03 |
| 25 | 1.245 | 93.9 | 8  | 5.95  | 0.49 | 0.51 | 0.02 |
|    |       |      | 16 | 11.90 | 0.98 | 1.01 | 0.03 |
|    |       |      | 24 | 17.85 | 1.47 | 1.52 | 0.05 |
| 30 | 1.239 | 91.4 | 8  | 5.79  | 0.69 | 0.71 | 0.02 |
|    |       |      | 16 | 11.59 | 1.38 | 1.42 | 0.04 |
|    |       |      | 24 | 17.38 | 2.06 | 2.13 | 0.06 |
| 35 | 1.232 | 88.8 | 8  | 5.63  | 0.90 | 0.93 | 0.03 |
|    |       |      | 16 | 11.26 | 1.79 | 1.85 | 0.06 |
|    |       |      | 24 | 16.88 | 2.69 | 2.78 | 0.08 |
| 40 | 1.225 | 86.0 | 8  | 5.45  | 1.12 | 1.16 | 0.03 |
|    |       |      | 16 | 10.90 | 2.24 | 2.31 | 0.07 |
|    |       |      | 24 | 16.35 | 3.36 | 3.47 | 0.10 |
| 45 | 1.217 | 83.0 | 8  | 5.26  | 1.36 | 1.40 | 0.04 |
|    |       |      | 16 | 10.52 | 2.72 | 2.81 | 0.08 |
|    |       |      | 24 | 15.78 | 4.08 | 4.21 | 0.13 |
| 50 | 1.208 | 79.7 | 8  | 5.06  | 1.62 | 1.67 | 0.05 |
|    |       |      | 16 | 10.11 | 3.24 | 3.34 | 0.10 |
|    |       |      | 24 | 15.17 | 4.86 | 5.01 | 0.15 |
| 55 | 1.199 | 76.2 | 8  | 4.83  | 1.90 | 1.96 | 0.06 |
|    |       |      | 16 | 9.66  | 3.80 | 3.92 | 0.12 |
|    |       |      | 24 | 14.50 | 5.71 | 5.88 | 0.18 |
| 60 | 1.189 | 72.4 | 8  | 4.59  | 2.21 | 2.28 | 0.07 |
|    |       |      | 16 | 9.17  | 4.42 | 4.56 | 0.14 |
|    |       |      | 24 | 13.76 | 6.63 | 6.84 | 0.21 |
| 65 | 1.178 | 68.1 | 8  | 4.32  | 2.55 | 2.63 | 0.08 |
|    |       |      | 16 | 8.63  | 5.11 | 5.26 | 0.16 |
|    |       |      | 24 | 12.95 | 7.66 | 7.90 | 0.24 |

TABLE I-continued

| RH (%) | SG | $G_w$ (%) | Wt (g) | $G_v$ (mL) | $H_v$ (mL) | $G_L$ (mL) | Glutaraldehyde (mL) |
|---|---|---|---|---|---|---|---|
| 70 | 1.165 | 63.3 | 8 | 4.01 | 2.94 | 3.03 | 0.09 |
|  |  |  | 16 | 8.02 | 5.87 | 6.05 | 0.18 |
|  |  |  | 24 | 12.04 | 8.81 | 9.08 | 0.27 |
| 75 | 1.151 | 57.8 | 8 | 3.67 | 3.37 | 3.48 | 0.10 |
|  |  |  | 16 | 7.33 | 6.75 | 6.96 | 0.21 |
|  |  |  | 24 | 11.00 | 10.12 | 10.43 | 0.31 |
| 80 | 1.134 | 51.5 | 8 | 3.26 | 3.88 | 4.00 | 0.12 |
|  |  |  | 16 | 6.53 | 7.76 | 8.00 | 0.24 |
|  |  |  | 24 | 9.79 | 11.65 | 12.01 | 0.36 |
| 85 | 1.114 | 43.8 | 8 | 2.78 | 4.49 | 4.63 | 0.14 |
|  |  |  | 16 | 5.56 | 8.99 | 9.27 | 0.28 |
|  |  |  | 24 | 8.33 | 13.48 | 13.90 | 0.42 |
| 90 | 1.089 | 34.2 | 8 | 2.17 | 5.26 | 5.43 | 0.16 |
|  |  |  | 16 | 4.34 | 10.53 | 10.85 | 0.33 |
|  |  |  | 24 | 6.50 | 15.79 | 16.28 | 0.49 |
| 95 | 1.055 | 21.1 | 8 | 1.34 | 6.31 | 6.51 | 0.20 |
|  |  |  | 16 | 2.67 | 12.62 | 13.01 | 0.39 |
|  |  |  | 24 | 4.01 | 18.94 | 19.52 | 0.59 |

Thus, to configure a humidity control device that maintains a desired relative humidity of about 35%, a user would preferably provide a humidity control solution having about 88.8% (by weight) glycerol.

Embodiments of the humidity control solutions, devices, and systems are effective over a range of temperatures, for example, from about −20° C. to about 50° C., or from about −15° C. to about 45° C. Embodiments of the humidity control solutions, devices, and systems maintain a humidity to within about a ±10% relative humidity range that includes the desired relative humidity, for example, about ±5% of the desired relative humidity percentage. For example, for a target relative humidity of 35%, embodiments of the solutions, devices, and systems maintain an actual relative humidity of from about 30% to about 40% (35%±5%).

As will be discussed below in connection with FIG. 7, the performance of the humidity control device is determined, in part, by the ratio of the total weight of the humidity control solution to the internal volume of the outside packaging. A user can provide a humidity control solution having a total weight, for example, of about 8 grams, about 16 grams, about 24 grams, or any other value appropriate for the internal volume of the outside packaging. If, for example, a user provides about 24 grams of a humidity control solution having about 88.8% (by weight) glycerol, the solution may comprise about 16.88 mL glycerol, about 2.69 mL water, and about 0.08 mL of a solution of 0.625% (by weight) glutaraldehyde. Thus, an embodiment of the humidity control solution would comprise about 16.88 mL glycerol and about 2.78 mL of an aqueous solution that is about 97% (by volume) water and 3% (by volume) of an aqueous 0.625% (by weight) glutaraldehyde solution.

Figure 5:
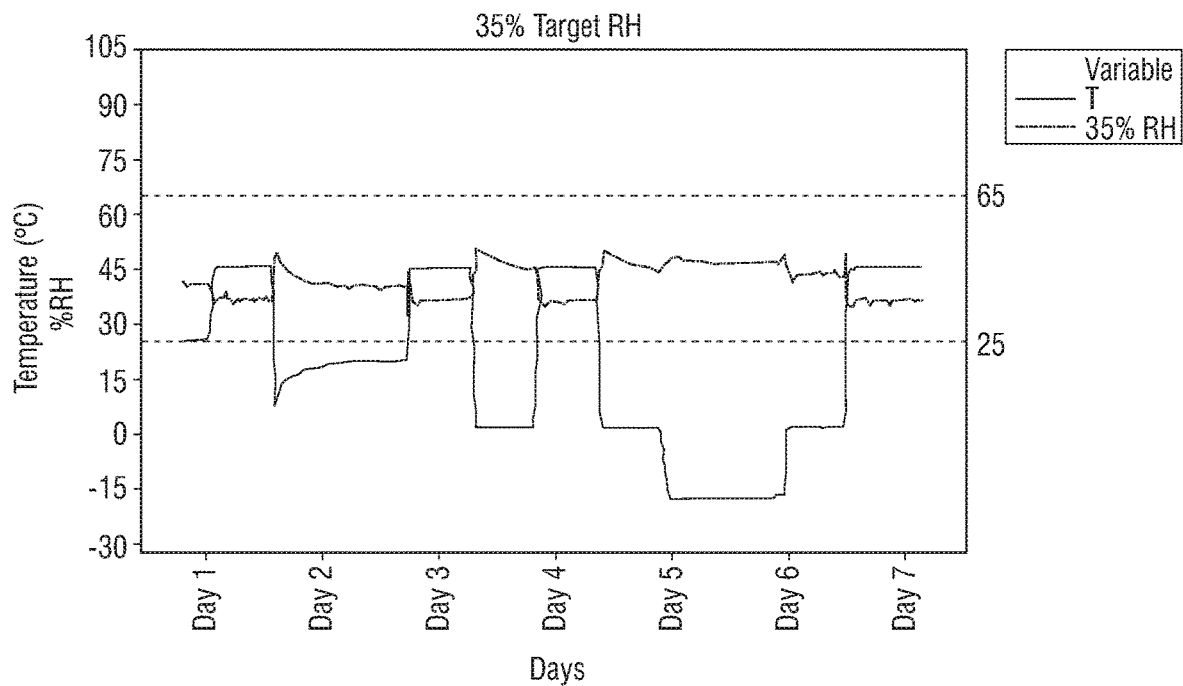
FIG. 5 is a graph illustrating a performance of an exemplary humidity control device having a target relative humidity of 35%.

FIG. 5 illustrates the relative humidity in an embodiment of a packaging system for storing a bioprosthetic device using 16 g of a solution with a target relative humidity of 35% across a range of temperatures. Relative humidity and temperature are on the same scale. Across the span of several days, the packaging system was exposed to temperatures from about −18° C. to about 45° C. At higher ambient temperatures, relative humidity within the packaging system decreased before returning to about 35%, while at lower ambient temperatures, relative humidity within the packaging system increased before returning to about 35%.

Figure 6:
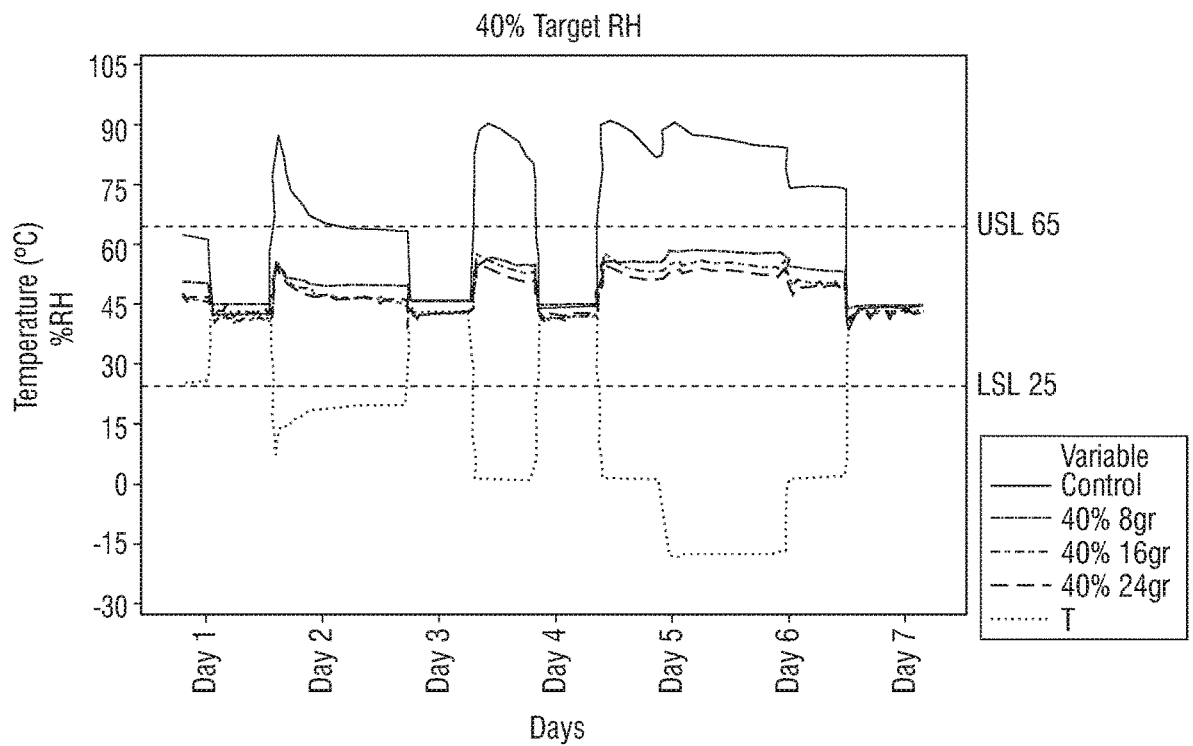
FIG. 6 is a graph illustrating a performance of three different masses or weights of an exemplary humidity control solution having a target relative humidity of 40%.

FIG. 6 illustrates embodiments of packaging systems including different amounts of a humidity control solution having a target relative humidity of 40% (prepared according to Table I). The total weights or masses of the humidity control solutions were 8 grams, 16 grams, and 24 grams. Relative humidity and temperature are on the same scale. As shown, the performance and response of the humidity control system to temperature changes improved with higher masses of the humidity control solution.

Figure 7:
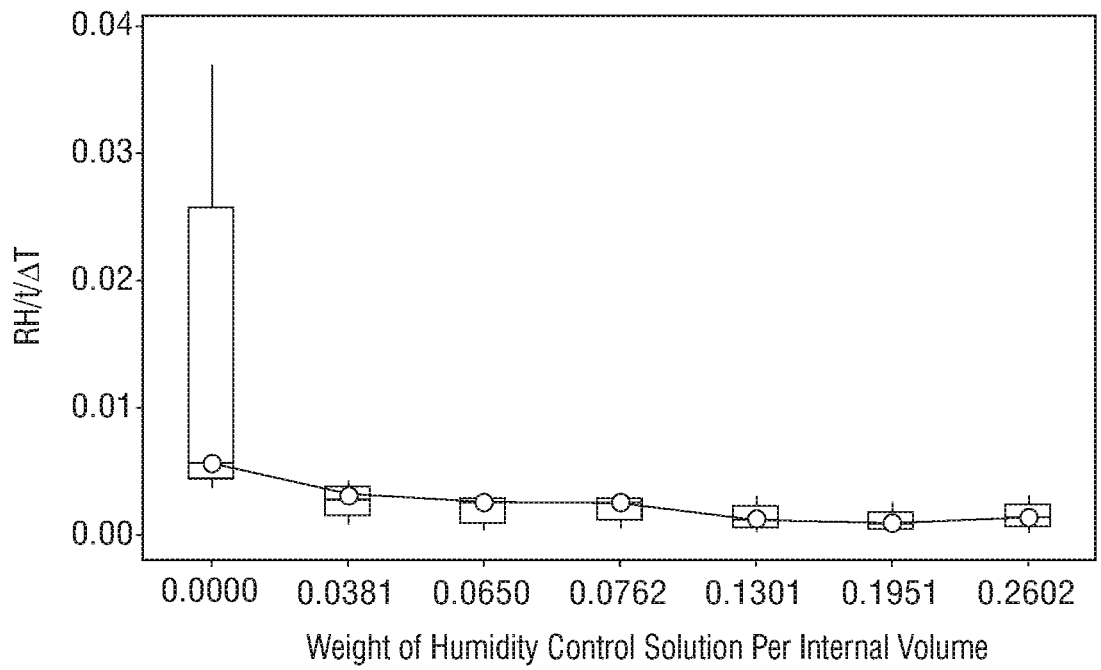
FIG. 7 is a graph illustrating a rate of change of relative humidity with change in temperature for different ratios of total weight of humidity control solution to internal volume of a sealed package in accordance with one embodiment.

With reference to FIG. 7, a boxplot of the rate of change of relative humidity for different ratios of total weight of humidity control solution to internal volume of the outside packaging ("ratio of total weight to volume") shows data from 8 g, 16 g, and 24 g of 35% target control solutions in two different size laminated foil pouches, plus a control sample. This graph provides an indication of the responsiveness of the packaging system. As shown, control of relative humidity improves as the ratio of total weight to volume increases. Thus, the performance of the humidity control device is determined, in part, by the ratio of total weight or mass to volume.

Figure 8:
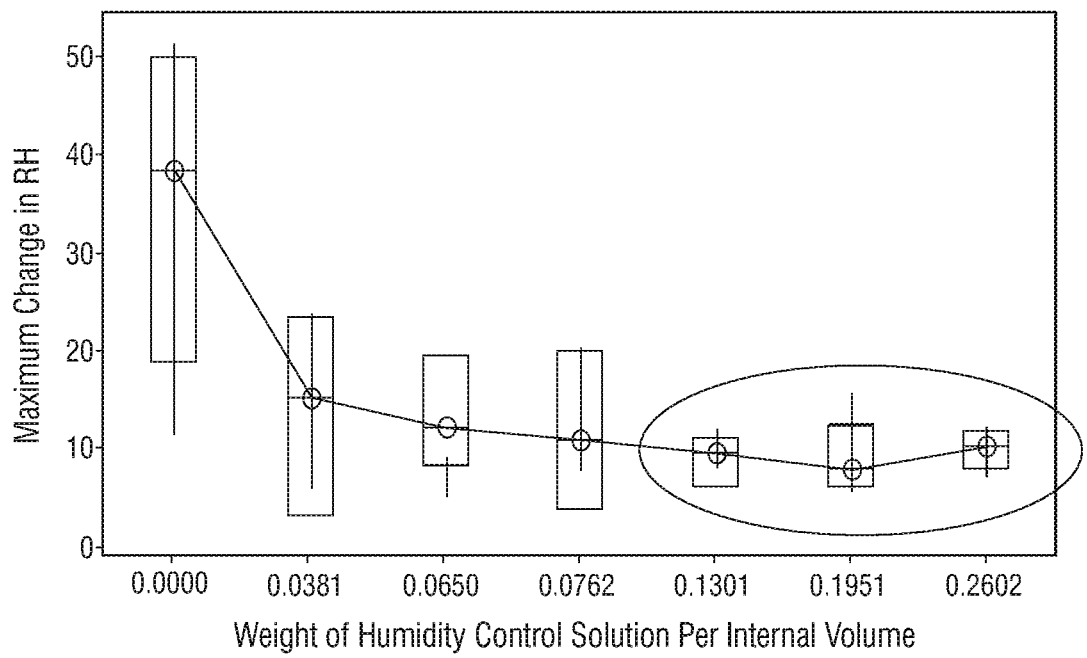
FIG. 8 is a graph illustrating the maximum percentage change of relative humidity for different ratios of total weight of humidity control solution to internal volume of a sealed package in accordance with one embodiment.

With reference to FIG. 8, a boxplot of the maximum change in relative humidity for different ratios of total weight of humidity control solution to internal volume of the package is shown for the same samples illustrated in FIG. 7. This graph provides an indication of the efficiency of the packaging system. As shown, control of relative humidity generally improves as the ratio of total weight to volume increases. However, with a ratio of total weight to volume of about 0.1 g per cubic inch (about 6 mg/mL) of the internal volume, the maximum change of relative humidity is about ±10% and further increases to the ratio of total weight to volume do not yield material improvements in the maximum change of relative humidity for the temperature range tested. Thus, a humidity control solution having a total weight to volume of about 0.1 g per cubic inch (about 6 mg/mL) of the internal volume or more can control relative humidity within about ±5% of the target equilibrium relative humidity.

FIG. 9 depicts an exemplary method 900 for storing a bioprosthetic device within a packaging system that maintains a target relative humidity range across a temperature range. In a first step 902, the internal volume of an outer packaging is determined. The internal volume can be determined using methods well known in the art. For example, the internal volume can be obtained experimentally or calculated from the geometry of the outer packaging.

The outer packaging is preferably sterile and, in an optional step (not shown), the outer packaging can be subjected to a terminal sterilization process or aseptic production.

Step 904 illustrates providing a humidity control solution having a weight within a gas-permeable enclosure to produce a humidity control device. The humidity control solution preferably includes glycerol. The gas-permeable enclosure can, for example, comprise a sealable pouch. In this case, the humidity control solution can be poured or injected into the pouch and the pouch can then be sealed with the humidity control solution within the gas-permeable enclosure. Of course, the humidity control solution can be provided within a gas-permeable enclosure by any other method well known in the art. In one embodiment, the gas-permeable enclosure has a water vapor transfer rate of from about 0.02 to about 0.07 grams per square inch per 24 hours (about 3-11 mg/cm$^2$/24 hr).

In one embodiment, an additional step (not shown) of selecting the target relative humidity from about 15% to about 95% can be performed. This selection step can be determined by the technical requirements of the bioprosthetic device. The selected target relative humidity will define the concentration of glycerol (by weight) in the humidity control solution. In one embodiment the concentration of glycerol ($G_w$) (by weight) in the humidity control solution is defined by the target relative humidity (RH) to be maintained according to Eq. 1, which is derived from the above equations.

$$G_w = 383(-0.189(RH)+19.9)^{0.0806} - 383 \qquad \text{Eq. 1}$$

For example, if the target storage relative humidity for the bioprosthetic device is about 35%, the concentration of glycerol in the humidity control solution can be about 88.8% (by weight). If the target storage relative humidity for the bioprosthetic device is about 65%, the concentration of glycerol in the humidity control solution can be about 68.1% (by weight).

In an alternative embodiment, the target relative humidity to be maintained within the internal volume of the outer packaging is determined by the concentration of glycerol in the humidity control solution, as provided in Eq. 2.

$$RH = -\frac{\left(\frac{G_w + 383}{383}\right)^{12.4} - 19.9}{0.189} \qquad \text{Eq. 2}$$

For example, for a humidity control solution with about 76.2% glycerol (by weight), the resulting humidity control device will maintain a target relative humidity of about 55%.

Referring back to FIG. 9, step 906 illustrates sealing the humidity control device and the bioprosthetic device within the internal volume of the outer packaging. This step can be accomplished by any sealing means, method, or modality. For example, if the outer packaging is provided as a pouch with a sealable flap 106, the humidity control device and bioprosthetic device would simply be placed within the internal volume before folding the flap over to seal the pouch. Other methods of sealing the humidity control device and the bioprosthetic device within the internal volume of the outer packaging include, for example, heat sealing, pressure sealing, adhesive sealing, and/or mechanical sealing.

Following this method, after the bioprosthetic device and the humidity control device are sealed within the internal volume of the outer packaging, in one embodiment the humidity control device will maintain the target relative humidity across a temperature range from about −18° C. to about 45° C.

It should be appreciated from the foregoing description that the packaging system that not only stores a bioprosthetic device in a relatively sterile environment, but that also maintains a relatively stable relative humidity therefor across a range of temperatures.

Unless defined otherwise, all technical and scientific terms used herein have the same meanings as commonly understood by one of ordinary skill in the art to which this embodiment belongs. Specific methods, devices, and materials are described, although any methods and materials similar or equivalent to those described can be used in the practice or testing of the present embodiment. It must be noted that as used herein, the singular forms "a," "an," and "the" include the plural reference unless the context clearly dictates otherwise. Thus, for example, a reference to "a bioprosthetic device" can be a reference to one or more bioprosthetic devices and include equivalents known to those skilled in the art.

Other objectives, features, and advantages of the present embodiments will become apparent from the following specific examples. The specific examples, while indicating specific embodiments, are provided by way of illustration only. Features, components, steps, etc. described in one embodiment can be included in other embodiments herein as well. Accordingly, various changes and modifications within the spirit and scope of the disclosure may become apparent to those skilled in the art from this detailed description, including the following non-limiting examples.

EXAMPLE

Three sets of seven humidity control solutions were prepared. Each humidity control solution in the first set had a total mass of 8 grams, each humidity control solution in the second set had a total mass of 16 grams, and each humidity control solution in the third set had a total mass of 24 grams.

For each of the three sets, the seven humidity control solutions were prepared according to TABLE I as follows: one with a concentration of glycerol sufficient to maintain a target relative humidity of about 20%, one with a target relative humidity of about 30%, one with a target relative humidity of about 40%, one with a target relative humidity of about 50%, one with a target relative humidity of about 60%, one with a target relative humidity of about 90%, and a Control solution with no glycerol.

To form the humidity control devices, the humidity control solutions were each poured into respective spunbonded polyolefin (Tyvek®, DuPont) pouches that were between 4.5 to 5.5 inches (11-14 cm) wide and between 5.5 to 7 inches (14-18 cm) long. Each pouch had a gas-permeable side and a non-permeable side. The gas-permeable side comprised an uncoated, medical-grade 3 mil (75 μm) HDPE COEX and the non-permeable side comprised a 100 gauge (25 μm) biaxially oriented film made of polyamide resin. The pouches had a water vapor transfer rate of about 0.03 grams per square inch (about 5 mg/cm$^2$) per 24 hours.

The humidity control devices were each sealed within respective laminated polymer/foil pouches, which had a water vapor transfer rate of about 0.001 grams per day per package. With this low water vapor transfer rate, the ambient relative humidity had little or no effect on the relative humidity within the sealed package's internal space. Relative humidity was measured using iButton temperature/humidity loggers (model DS1923, Maxim Integrated, San Jose, Calif.).

The three sets of packaging systems were then placed within a test chamber where they were subjected to the following temperature profile: 25° C. for 10 hours, followed by 45° C. for 24 hours, followed by 15-20° C. for 50 hours, followed by 45° C. for 24 hours, followed by 1° C. for 24 hours, followed by 45° C. for 24 hours, followed by 1° C. for 24 hours, followed by −18° C. for 48 hours, followed by 1° C. for 24 hours, followed by 45° C. for the 32 hours.

The packaging systems successfully controlled the relative humidity across the temperature profile. The packaging systems exhibited two-way control of the relative humidity—adding and removing water vapor to control for any target humidity. As expected, the target humidity was not maintained within the internal spaces by the Control systems, which did not contain glycerol.

The temperature was found to have an inverse effect on the equilibrium relative humidity. Thus, the equilibrium relative humidity was found to be higher at lower temperatures and lower at higher temperatures.

Comparing the packaging systems having the same target relative humidity but different ratios of total weight to volume showed that performance and response to temperature shocks is improved with humidity control solutions having a higher ratio of total weight to volume.

Table II sets forth results from experiments including data for a Control system and packaging systems having a target relative humidities of 30% and 40%, where "Mass" is the mass of the control solution in grams, "Volume" is the internal volume of the package in cubic inches (123 in$^3$≈2 L), "m/V" is the mass to volume ratio in g/in$^3$ (1 g/in$^3$≈0.06 g/mL), "$\Delta T_n$" is the nth temperature change, "$\Delta$RH" is the change in relative humidity at steady state, "$\Delta t$" is the time to change the temperature, "RH/t" is the rate of change of relative humidity, and "RH/t/$\Delta T$" is the rate of change of relative humidity per temperature change.

TABLE II

| Target RH | 30% | 30% | 30% | 40% | 40% | 40% | Control |
|---|---|---|---|---|---|---|---|
| Mass (g) | 8 | 16 | 24 | 8 | 16 | 24 | 0 |
| Volume (in$^3$) | 123 | 123 | 123 | 123 | 123 | 123 | 123 |
| m/V (g/in$^3$) | 0.065 | 0.13 | 0.195 | 0.065 | 0.13 | 0.195 | 0 |
| $\Delta T_1$ | 38 | 38 | 38 | 38 | 38 | 38 | 38 |
| $\Delta$RH | 10 | 10 | 12 | 10 | 16 | 13 | 45 |
| $\Delta t$ (min) | 165 | 165 | 195 | 150 | 165 | 165 | 180 |
| RH/t | 0.061 | 0.061 | 0.062 | 0.067 | 0.097 | 0.079 | 0.25 |
| RH/t/$\Delta T$ | 0.0016 | 0.0016 | 0.0016 | 0.0018 | 0.0026 | 0.0021 | 0.0066 |
| $\Delta T_2$ | 25 | 25 | 25 | 25 | 25 | 25 | 25 |
| $\Delta$RH | 7 | 2 | 4 | 6 | 7 | 6 | 23 |
| $\Delta t$ (min) | 60 | 45 | 45 | 45 | 45 | 45 | 120 |
| RH/t | 0.117 | 0.044 | 0.089 | 0.133 | 0.156 | 0.133 | 0.192 |
| RH/t/$\Delta T$ | 0.0047 | 0.0018 | 0.0036 | 0.0053 | 0.0062 | 0.0053 | 0.0077 |
| $\Delta T_3$ | 44 | 44 | 44 | 44 | 44 | 44 | 44 |
| $\Delta$RH | 9 | 11 | 10.5 | 10.5 | 18 | 15 | 45 |
| $\Delta t$ (min) | 195 | 165 | 180 | 180 | 165 | 210 | 165 |
| RH/t | 0.046 | 0.067 | 0.058 | 0.058 | 0.109 | 0.071 | 0.273 |
| RH/t/$\Delta T$ | 0.001 | 0.0015 | 0.0013 | 0.0013 | 0.0025 | 0.0016 | 0.0062 |
| $\Delta T_4$ | 44 | 44 | 44 | 44 | 44 | 44 | 44 |
| $\Delta$RH | 11 | 12 | 9 | 11 | 13.5 | 15 | 42 |
| $\Delta t$ (min) | 210 | 210 | 165 | 180 | 180 | 165 | 165 |
| RH/t | 0.052 | 0.057 | 0.055 | 0.061 | 0.075 | 0.091 | 0.255 |
| RH/t/$\Delta T$ | 0.0012 | 0.0013 | 0.0012 | 0.0014 | 0.0017 | 0.0021 | 0.0058 |
| $\Delta T_5$ | 44 | 44 | 44 | 44 | 44 | 44 | 44 |
| $\Delta$RH | 10 | 13 | 12 | 14 | 16.5 | 15 | 14 |
| $\Delta t$ (min) | 225 | 180 | 165 | 285 | 195 | 210 | 165 |
| RH/t | 0.044 | 0.072 | 0.073 | 0.049 | 0.085 | 0.071 | 0.085 |
| RH/t/$\Delta T$ | 0.001 | 0.0016 | 0.0017 | 0.0011 | 0.0019 | 0.0016 | 0.0019 |
| $\Delta T_6$ | 16 | 16 | 16 | 16 | 16 | 16 | 16 |
| $\Delta$RH | 3 | 2 | 2 | 3 | 3 | 1 | 12 |
| $\Delta t$ (min) | 210 | 225 | 180 | 255 | 255 | 225 | 270 |
| RH/t | 0.014 | 0.009 | 0.011 | 0.012 | 0.012 | 0.004 | 0.044 |
| RH/t/$\Delta T$ | 0.0009 | 0.0006 | 0.0007 | 0.0007 | 0.0007 | 0.0003 | 0.0028 |
| $\Delta T_7$ | 16 | 16 | 16 | 16 | 16 | 16 | 16 |
| $\Delta$RH | 10 | 14 | 4 | 3 | 7 | 6 | 1 |
| $\Delta t$ (min) | 300 | 300 | 300 | 285 | 315 | 315 | 300 |
| RH/t | 0.033 | 0.047 | 0.013 | 0.011 | 0.022 | 0.019 | 0.003 |
| RH/t/$\Delta T$ | 0.0021 | 0.0029 | 0.0008 | 0.0007 | 0.0014 | 0.0012 | 0.0002 |

The weight of the humidity control solution was found to have no effect on the equilibrium relative humidity for the same concentration. In other words, for humidity control solutions with a given concentration of glycerol, the 8 gram, 16 gram, and 24 gram systems had the same equilibrium relative humidity.

With reference again to FIG. 5, a packaging system with a target relative humidity of 35% was found to have a Process Capability Index of about 1.45, where the Upper Specification Limit was 65% and the Lower Specification Limit was 25%.

With reference to TABLE II and to FIGS. 7 and 8, both the maximum change in relative humidity and the rate of change of relative humidity improved as the ratio of total weight to volume increased. However, with a total weight or mass to volume of about 0.1 g per cubic inch (about 6 mg/mL) of the internal volume, the maximum change in relative humidity was about ±10% and further increases to the ratio of total weight or mass to volume did not yield material improvements.

Certain embodiments have been described in detail herein, which persons skilled in the art will appreciate can be modified without departing from the scope of the disclosure, which is defined only by the following claims.

What is claimed is:

1. A packaging system for storing a bioprosthetic device, the packaging system comprising:
    a sealed package defining an internal space;
    at least one bioprosthetic device disposed within the internal space; and
    at least one humidity control device disposed within the internal space, the at least one humidity control device comprising:
        an at least partially gas-permeable enclosure defining an enclosed space, and a humidity control solution comprising glycerol, the humidity control solution disposed in the enclosed space defined by the at least partially gas-permeable enclosure;
    wherein the at least one humidity control device maintains a relative humidity range about a target relative humidity within the internal space of the sealed package across a temperature range.

2. The packaging system of claim 1, wherein the sealed package has a water vapor transfer rate of less than about 2 milligrams per day.

3. The packaging system of claim 1, wherein the at least one humidity control device maintains the relative humidity range within a tolerance of about +−0.10% of the target relative humidity.

4. The packaging system of claim 1, wherein at least a portion of the at least partially gas-permeable enclosure comprises a gas-permeable membrane.

5. The packaging system of claim 4, wherein the gas-permeable membrane has a water vapor transfer rate of from about 3 to about 10 mg/cm$^2$ per 24 hours.

6. The packaging system of claim 4, wherein:
    the gas-permeable membrane has a surface area;
    the internal space of the sealed package has an internal volume; and
    a ratio of the surface area of the gas-permeable membrane to the internal volume of the internal space of the sealed package is from about 6 to about 30 mg/mL.

7. The packaging system of claim 4, wherein the gas-permeable membrane has an average porosity of about 8 to about 36 Gurley units.

8. The packaging system of claim 1, wherein the bioprosthetic device comprises a bioprosthetic tissue that has a reduced water content of about 25% by weight or less.

9. The packaging system of claim 8, wherein:
    the bioprosthetic device is a heart valve; and
    the bioprosthetic tissue forms leaflets of the heart valve.

10. A packaging system for storing a bioprosthetic device, the packaging system comprising:
    a sealed package defining an internal space; at least one bioprosthetic device disposed within the internal space; and
    at least one humidity control device disposed within the internal space, the humidity control device comprising:
        an at least partially gas-permeable enclosure defining an enclosed space, and a humidity control solution comprising glycerol, the humidity control solution disposed in the enclosed space defined by the at least partially gas-permeable enclosure.

11. The packaging system of claim 10, wherein:
    the humidity control solution has a total weight;
    the internal space of the sealed package has an internal volume; and
    a ratio of the total weight of the humidity control solution to the internal volume of the internal space of the sealed package is at least about 6 mg/mL.

12. The packaging system of claim 10, wherein:
    the at least one humidity control device releases water vapor into the internal space when a relative humidity within the internal space decreases due to higher ambient temperatures; and
    the at least one humidity control device absorbs water vapor from the internal space when the relative humidity within the internal space increases due to lower ambient temperatures.

13. The packaging system of claim 10, wherein:
    the humidity control solution further comprises an aqueous solution;
    the glycerol is provided in a concentration of from about 34% to about 96% (by weight) of the humidity control solution; and
    the aqueous solution is provided in a concentration of from about 4% to about 66% (by weight) of the humidity control solution.

14. The packaging system of claim 10, wherein the at least one humidity control device maintains a target relative humidity within the internal space of the sealed package across a temperature range.

15. The packaging system of claim 14, wherein the temperature range is from about 18° C. to about 45° C.

16. The packaging system of claim 14, wherein the target relative humidity is from about 15% to about 95%.

17. The packaging system of claim 14, wherein a concentration of the glycerol ($G_W$) (by weight) in the humidity control solution is substantially related to the target relative humidity (RH) according to Eq. 1:

$$G_w=383(-0.189(RH)+19.9)^{0.0806}-383 \qquad \text{Eq. 1.}$$

18. The packaging system of claim 14, wherein the target relative humidity (RH) is substantially related to a concentration of the glycerol ($G_W$) (by weight) in the humidity control solution according to Eq. 2:

$$RH = -\frac{\left(\frac{G_w+383}{383}\right)^{12.4}-19.9}{0.189}. \qquad \text{Eq. 2}$$

19. The packaging system of claim 14, wherein the at least one humidity control device maintains the target relative humidity within a tolerance of about ±10%.

20. The packaging system of claim 10, wherein the humidity control solution further comprises a microbicidal agent.

21. The packaging system of claim 20, wherein the microbicidal agent comprises an aqueous solution comprising about 97% (by volume) water and about 3% (by volume) of a solution of about 0.625% (by weight) glutaraldehyde.

22. A method of storing at least one bioprosthetic device within a packaging system, the method comprising the steps of:
    selecting a target relative humidity to be maintained within an outer packaging of the packaging system across a temperature range;
    providing at least one humidity control device comprising a humidity control solution, wherein the humidity control solution comprises glycerol and is disposed within an at least partially gas-permeable enclosure; and
    sealing the at least one humidity control device and the at least one bioprosthetic device within the outer packaging.

23. The method of claim 22, wherein selecting the target relative humidity comprises selecting a target relative humidity from about 15% to about 95%.

24. The method of claim 22, wherein a concentration of the glycerol ($G_W$) (by weight) in the humidity control solution is substantially related to the target relative humidity (RH) according to Eq. 1:

$$G_w = 383(-0.189(RH)+19.9)^{0.0806} - 383 \qquad \text{Eq. 1.}$$

25. The method of claim 22, wherein the target relative humidity (RH) is substantially related to a concentration of the glycerol ($G_W$) (by weight) in the humidity control solution according to Eq. 2:

$$RH = -\frac{\left(\frac{G_w + 383}{383}\right)^{12.4} - 19.9}{0.189}. \qquad \text{Eq. 2}$$

26. The method of claim 22, wherein:
the humidity control solution has a total weight;
the outer packaging, after sealing, has an internal volume; and
a ratio of the total weight of the humidity control solution to the internal volume of the outer packaging after sealing is at least about 6 mg/mL.

27. The method of claim 22, wherein the temperature range is from about −18° C. to about 45° C.

28. The packaging system of claim 22, wherein the at least one humidity control device maintains the target relative humidity within a tolerance of about ±10%.

\* \* \* \* \*